(12) United States Patent
Hu et al.

(10) Patent No.: US 10,392,362 B2
(45) Date of Patent: Aug. 27, 2019

(54) METHOD FOR SYNTHESIZING LACTIDE BY MEANS OF CATALYSIS OF LACTID ACID

(71) Applicant: The Hong Kong Research Institute of Textiles and Apparel Limited, Kowloon (HK)

(72) Inventors: Yunzi Hu, Kowloon (HK); Carol Sze Ki Lin, Kowloon (HK); Walid Daoud, Kowloon (HK)

(73) Assignee: The Hong Kong Research Institute of Textiles and Apparel Limited, Kowloon (HK)

( * ) Notice: Subject to any disclaimer, the term of this patent is extended or adjusted under 35 U.S.C. 154(b) by 0 days.

(21) Appl. No.: 16/078,674

(22) PCT Filed: Mar. 1, 2016

(86) PCT No.: PCT/CN2016/075167
§ 371 (c)(1),
(2) Date: Aug. 22, 2018

(87) PCT Pub. No.: WO2017/143622
PCT Pub. Date: Aug. 31, 2017

(65) Prior Publication Data
US 2019/0047976 A1    Feb. 14, 2019

(30) Foreign Application Priority Data

Feb. 24, 2016  (CN) .......................... 2016 1 0102406

(51) Int. Cl.
*C07D 319/00* (2006.01)
*C07D 319/12* (2006.01)
(Continued)

(52) U.S. Cl.
CPC ............ *C07D 319/12* (2013.01); *B01J 23/06* (2013.01); *B01J 35/0013* (2013.01); *B01J 35/10* (2013.01)

(58) Field of Classification Search
CPC .......... C07D 319/12; B01J 35/10; B01J 23/06
(Continued)

(56) References Cited

U.S. PATENT DOCUMENTS 5,053,522 A   10/1991  Muller
5,247,058 A    9/1993  Gruber et al.
(Continued)

FOREIGN PATENT DOCUMENTS

CN   1488628 A   4/2004
CN   1583740 A   2/2005
(Continued)

OTHER PUBLICATIONS

Wikipedia , Zinc Oxide, Sep. 2015, p. 1-22 . (Year: 2015).*
(Continued)

*Primary Examiner* — Taylor V Oh
(74) *Attorney, Agent, or Firm* — Barlow, Josephs & Holmes, Ltd.

(57) ABSTRACT

The present invention relates to a method for the catalytic synthesis of lactide from lactic acid. The method relates to the synthesis of lactide from lactic acid under the catalysis of a zinc oxide nanoparticle aqueous dispersion as a catalyst. The present invention has four technical characteristics: I. the zinc oxide nanoparticle aqueous dispersion catalyst has a sufficient surface area, and the size of nanoparticles is merely 30-40 nm, providing a sufficient contact area between the substrate (lactic acid) and the catalyst; II. the new catalyst has a milder catalytic effect on polymerization, allowing the molecular weight distribution of a prepolymer within a range of 400-1500 g/mol, which is advantageous for
(Continued)

depolymerization to proceed; III. the new catalyst is stable, thus avoiding oxidation or carbonization in a high temperature reaction; and IV. the new catalyst has a low toxicity and a small threat to human health.

8 Claims, 5 Drawing Sheets

(51) Int. Cl.
  *B01J 23/06* (2006.01)
  *B01J 35/00* (2006.01)
  *B01J 35/10* (2006.01)
(58) Field of Classification Search
  USPC .......................................................... 549/274
  See application file for complete search history.

(56) References Cited

U.S. PATENT DOCUMENTS

| | | |
|---|---|---|
| 5,274,127 A | 12/1993 | Sinclair et al. |
| 5,357,035 A | 10/1994 | Gruber et al. |
| 6,005,067 A | 12/1999 | Gruber et al. |
| 6,277,951 B1 | 8/2001 | Gruber et al. |
| 6,326,458 B1 | 12/2001 | Gruber et al. |
| 2005/0222379 A1 | 10/2005 | Matsuo et al. |
| 2011/0155557 A1 | 6/2011 | Coszach et al. |
| 2012/0302724 A1 | 11/2012 | Hong et al. |

FOREIGN PATENT DOCUMENTS

| | | | |
|---|---|---|---|
| CN | 1594313 A | | 3/2005 |
| CN | 1951933 A | | 4/2007 |
| CN | 102863420 A | * | 1/2013 |
| WO | 2010105143 A2 | | 9/2010 |

OTHER PUBLICATIONS

Cheng, Chao: "The Selection of Catalyst to Prepare Lactide and an Initial Analysis of Reaction Mechanism", College of Bioengineering, Chongqing University (A), China Master's Theses Full-Text Database, Jan. 31, 2006 (Jan. 31, 2006), chapter 2, section 2.2.4, and chapter 3.

Chen, Jia et al, "Advances of Catalysts for Synthesizing Lactide", Chemical Research and Application, vol. 19, No. 4, Apr. 30, 2007 (Apr. 30, 2007), p. 358, section 2.1.

Qiu, Kui et al., "On Lactide Synthesis Method and Condition of Reaction", Journal of Chongqing University of Science and Technology (Natural Sciences Edition), vol. 8, No. 4, Dec. 31, 2006 (Dec. 31, 2006), pp. 16-18.

* cited by examiner

METHOD FOR SYNTHESIZING LACTIDE BY MEANS OF CATALYSIS OF LACTID ACID

TECHNICAL FIELD

The present invention relates to the technical field of the preparation of biodegradable polymers, and more specifically relates to a method for the catalytic synthesis of lactide from lactic acid.

BACKGROUND ART

The techniques for the synthesis of lactide from lactic acid has been developed for several decades and the synthesis method thereof has been described in numerous patents, such as U.S. Pat. Nos. 5,053,522 A, 5,247,058 A, 5,357,035 A, 6,005,067 A, 6,277,951 B1, 6,326,458 B1, 5,274,127 A, US 20050222379 A1, US 20120302724 A1, US 20110155557 A1, CN 1951933 A, CN 1594313 A, CN 1488628 A, and WO 2010105143 A2. At the present stage, methods mainly used in industrial productions relate to heating at high temperatures and using tin-based chemicals as catalysts (such as tin (II) 2-ethylhexanoate and tin chloride) in a vacuum environment. In order to avoid the oxidation of the reactants under high temperature conditions (≥180° C.), the chemical reaction is usually carried out in an inert gas atmosphere (e.g., nitrogen).

The synthesis process involves two reactions as below:

1) Oligomerization: the lactic acid monomer undergoes a dehydration polymerization reaction to form an oligomer/prepolymer.

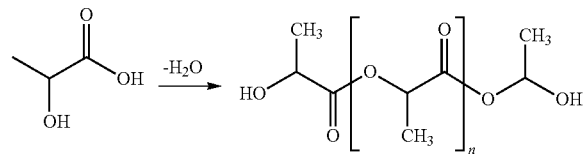

2) Depolymerization: the oligomer/prepolymer is depolymerized into cyclic dimer lactide.

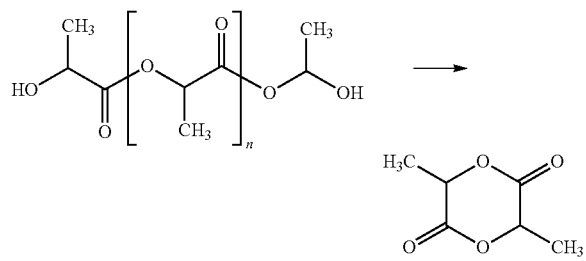

In the depolymerization process, the reaction conditions of a high temperature and a low pressure can cause the oligomer to partially depolymerize and at the same time, causes the remaining oligomer to further polymerize into a polymer with a higher molecular weight. Conventional tin-based catalysts are more conducive to polymerization rather than depolymerization, resulting in increased difficulty in the synthesis and separation of lactide. Therefore, the production yield of lactide synthesis of a conventional method is usually merely 50-70%. For example, U.S. Pat. No. 5,053,522 A describes a method for the synthesis of lactide with a tin-based catalyst, in which a high temperature of 200-260° C. is required to separate the lactide product, and the production yield is 69%. In a single batch production in U.S. Pat. No. 5,274,127, lactide production yield is 56.8%. In addition, the low catalytic efficiency of other metal compounds for polymerization and degradation leads to a decrease in the production yield of lactide (<70%). For example, zinc oxide particles are applied in US Patent US 201203027 A1, and the lactide product is obtained by distillation separation at a high temperature of 230-240° C., with the production yield obtained being lower than 72%. Therefore, traditional lactide synthesis methods have a low production yield and need to be further optimized and improved.

SUMMARY OF THE INVENTION

The technical problem to be solved by the present invention is to provide a method for the catalytic synthesis of lactide from lactic acid, which solves the problems of the prior art—difficulty in the synthesis and separation of lactide, low production yield of lactide, etc.

The technical solution of the present invention to solve the above-mentioned technical problems is to provide a method for the catalytic synthesis of lactide from lactic acid, involving the synthesis of lactide from lactic acid under the efficient catalysis of a zinc oxide nanoparticle aqueous dispersion as a catalyst by optimized reaction conditions and process.

In the method for the catalytic synthesis of lactide from lactic acid as provided by the present invention, said zinc oxide nanoparticle aqueous dispersion is a dispersion of zinc oxide nanoparticles in water, and the particle size of the zinc oxide nanoparticles is 30-40 nm, and the mass percentage of the zinc oxide nanoparticles is 20%. The present invention has four technical characteristics: I. the zinc oxide nanoparticle aqueous dispersion catalyst has a sufficient surface area, and the size of nanoparticles is merely 30-40 nm, providing a sufficient contact area between the substrate (lactic acid) and the catalyst; II. the new catalyst has a mild catalytic effect on polymerization, allowing the molecular weight distribution of a prepolymer within a range of 400-1500 g/mol, which is advantageous for depolymerization to proceed; III. the new catalyst is stable, thus avoiding oxidation or carbonization in a high temperature reaction; and IV. the new catalyst has a low toxicity and poses a small threat to human health.

In the present invention, the reaction process of the catalytic synthesis of lactide from lactic acid can be carried out using an apparatus as shown in FIG. 1, the apparatus comprising an oil bath (1), a round-bottom flask reactor (2) and a condenser (3), dehydration and distillation products are received by a collector (4), collector (4) is connected with a cold trap (5) and an oil pump (6); a thermo-controller (7) and a heating plate (8) are used to detect and control the heating temperature of the oil bath, and a thermometer (9) for detecting the temperature of a fraction. The pressure in a sealed reaction system is detected by a pressure monitoring detector (10) and controlled by a gas valve (11).

The method for the catalytic synthesis of lactide from lactic acid as provided by the present invention comprises the following steps:

S100. Dehydration: lactic acid and a catalyst are mixed at a ratio under the conditions of 60-80° C. and 60 kPa, and subjected to a dehydration reaction for 2 hours to remove free water from the lactic acid to obtain a dehydration product;

S200. Polymerization: said dehydration product is subjected to a polymerization reaction for 3 hours under the conditions of 120-150° C. and 10 kPa to obtain an oligomer; and S300. Depolymerization: said oligomer is subjected to a depolymerization reaction for 3-5 hours under the conditions of 170-220° C. and 1-3 kPa.

With this method, the production yield of lactide synthesis can be increased to 90% or more. The reaction time of each step depends on the specific quantity of the raw material (lactic acid). In the examples of this patent, 50 ml of L-lactic acid (86%) is used as a raw material for each example. The resulting crude lactide is purified by performing recrystallization in ethyl acetate once or twice.

In the method for the catalytic synthesis of lactide from lactic acid as provided by the present invention, the addition amount of said catalyst in step S100 is 0.3-0.6% by weight of said lactic acid.

Implementing the present invention results in the following beneficial effects:

1) Higher synthesis efficiency. The zinc oxide nanoparticle aqueous dispersion as a novel catalyst has a larger surface area than conventional solid or liquid catalysts. Therefore, the catalyst can be in better contact with lactic acid, improving the catalytic efficiency. Moreover, in the polymerization reaction and depolymerization reaction, zinc oxide nanoparticles can promote the equilibrium of the reaction to the depolymerization reaction, thereby increasing the synthesis yield and increasing the production yield to about 90%;

2) Lower energy consumption. The high catalytic efficiency of the zinc oxide nanoparticles facilitates the depolymerization and distillation purification, which can result in obtaining lactide by separation at a lower temperature and within a shorter time (170-220° C., 3-5 hours), reducing energy consumption, as compared with traditional methods (180-250° C., 8-10 hours). Furthermore, the lower temperature can avoid the racemization and carbonization of the prepolymer and lactide, improving the optical purity of the product;

3) Lower safety risk. The catalyst in this new method is less toxic than conventional tin-based catalysts. Besides, the risk of inhalation of conventional solid particles of heavy metal catalysts into human bodies can be avoided by the dispersion form.

BRIEF DESCRIPTION OF THE DRAWINGS

In order to more clearly illustrate the technical solutions in the embodiments of the present invention or in the prior art, the drawings used in the description of the embodiments or the prior art will be briefly described below. Obviously, the drawings in the following description are merely for some embodiments of the present invention, and a person skilled in the art would be able to obtain other drawings according to these drawings without involving any inventive effort.

FIG. 3 is a set of photographs of Examples 3 and 5 recorded during depolymerization.

DETAILED DESCRIPTION OF EMBODIMENTS

The technical solutions in the embodiments of the present invention will be clearly and completely described below in conjunction with examples.

EXAMPLE

1. Raw Material

In this example, commercial lactic acid (86%, 50 ml per group) supplied by Sigma is used as a raw material.

2. Catalyst

The catalyst used in each example is shown in Table 1. In Example 1, a group without a catalyst is set as a control group. The addition amounts of tin(II) 2-ethylhexanoate (also known as stannous octoate) in Examples 2 and 3 are respectively 0.3 wt % and 0.6 wt % of the weight of the raw material. 0.3 wt % and 0.6 wt % of a zinc oxide nanoparticle (30-40 nm) aqueous dispersion (20 wt %, US Research Nanomaterials) are respectively used as catalysts in Examples 4 and 5.

All chemicals are used directly without pretreatment.

TABLE 1

Catalysts used in Examples 1-5

| Example No. | Catalyst | Catalyst amount A (wt %) |
| --- | --- | --- |
| 1 | None | — |
| 2 | Tin(II) 2-ethylhexanoate | 0.3 |
| 3 |  | 0.6 |
| 4 | zinc oxide nanoparticle aqueous dispersion (30-40 nm, 20 wt %) | 0.3 |
| 5 |  | 0.6 |

3. Reaction Process

Figure 1:
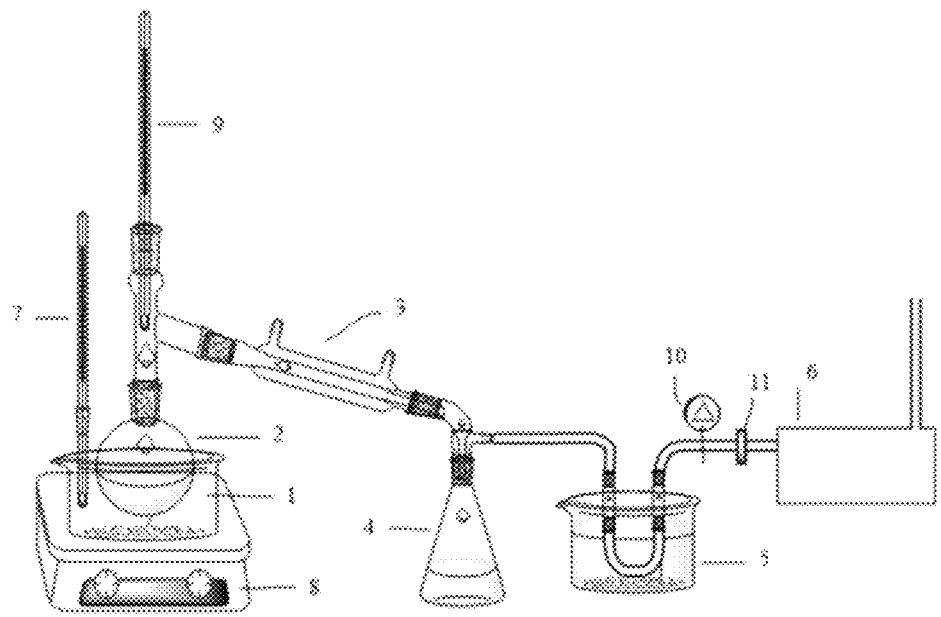
FIG. 1 is a structural schematic diagram of a reaction apparatus for implementing the present invention; (1) oil bath, (2) round-bottom flask reactor, (3) condenser, (4) collector, (5) cold trap, (6) oil pump, (7) thermo-controller, (8) heating plate, (9) thermometer, (10) pressure detector, and (11) gas valve.
Figure 2:
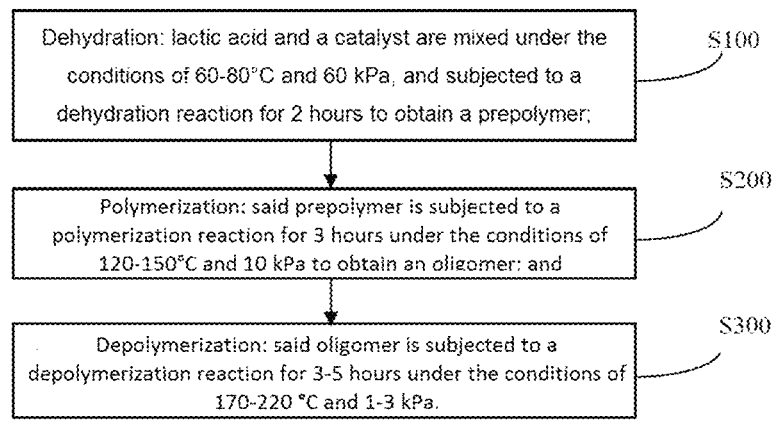
FIG. 2 is a flow chart of an optimized reaction process for the catalytic synthesis lactide from lactic acid of the present invention.
Figure 3A:
FIG. 3(A) is the case where the reaction temperature of Example 3 is 200° C.
Figure 3B:
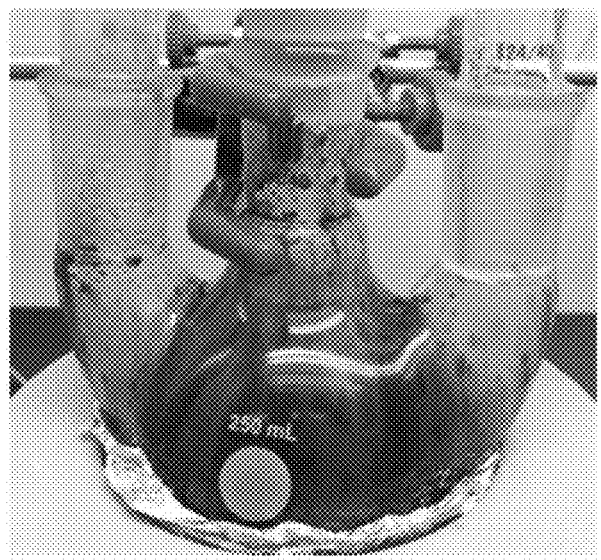
FIG. 3(B) is the case where the reaction temperature of Example 3 is 250° C.
Figure 3C:
FIG. 3(C) is the case where the reaction temperature of Example 5 is 200° C.
Figure 3D:
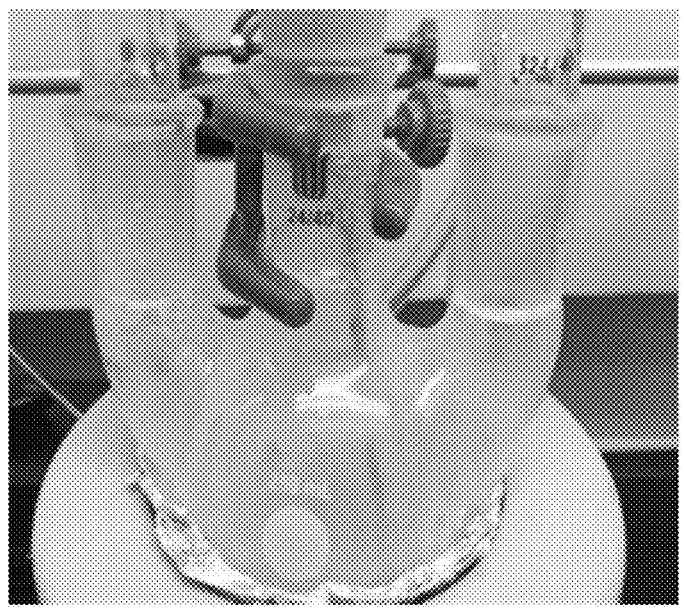
FIG. 3(D) is the case where the reaction temperature of Example 5 is 220° C.

FIG. 2 shows a process flow chart of the process for the catalytic synthesis lactide from lactic acid of the present invention. As shown in FIG. 2, lactic acid and a catalyst are firstly added to a round-bottom flask (250 ml), and the lactic acid and the catalyst are uniformly mixed by means of a magnetic stirrer under the conditions of 60-80° C. and 60 kPa, and reacted for 2 hours to remove free water therefrom. Then, the heating temperature is gradually adjusted to 120-150° C., and the reactants are subjected to a polymerization reaction for 3 hours under 10 kPa conditions to obtain an oligomer. Finally, depolymerization is performed at 170° C. for a period of time (about 20-30 minutes), the temperature is then increased and the pressure reduced gradually, and under the conditions of 1-3 kPa and 170-220° C., lactide is continuously distilled out until no more product is formed.

The weights of the products collected in the condenser and collector are measured by an electronic balance. Equation 1 and Equation 2 are used to calculate the conversion yield and production yield of the product.

Conversion yield=(Mass of lactide produced)/(Mass of lactide added)*100%  Equation 1

Production yield=(Mass of lactide produced in reality)/(Mass of lactide produced in theory)*100%  Equation 2

The molecular weight of the oligomer/prepolymer is detected by a GPC method (Gel Permeation Chromatography, Waters, USA). The purity of lactide is determined by 1H-NMR.

4. Results

1) Molecular Weight of Oligomer/Prepolymer and Polymer

TABLE 2

The molecular weight of prepolymer and polymer in Examples 1-5

| Example No. | Catalyst | Molecular weight of prepolymer (g mol$^{-1}$) | Molecular weight of polymer (g mol$^{-1}$) |
| --- | --- | --- | --- |
| 1 | None | 1169 | 1719 |
| 2 | Tin(II) 2-ethylhexanoate (0.3 wt %) | 1877 | 8839 |
| 3 | Tin(II) 2-ethylhexanoate (0.6 wt %) | 2354 | 11875 |
| 4 | Zinc oxide nanoparticle aqueous dispersion (30-40 nm, 0.3 wt %) | 877 | 3352 |
| 5 | Zinc oxide nanoparticle aqueous dispersion (30-40 nm, 0.6 wt %) | 684 | 3066 |

From the above results, it can be seen that as compared with zinc oxide nanoparticles, tin (II) 2-ethylhexanoate is more conducive in increasing the molecular weights of the prepolymer and polymer under the conditions of a reaction temperature of 150-220° C. Where zinc oxide nanoparticle are used as a catalyst, the molecular weight of the synthesized prepolymer is less than 900 g/mol, and the prepolymer easier to depolymerize into lactide than the prepolymers with molecular weights exceeding 1800 g/mol as obtained in Examples 2 and 3. After rising the temperature to 220° C. in the depolymerization reaction, the molecular weight of the polymer obtained under the catalysis of tin(II) 2-ethylhexanoate is greater than 8000 g/mol; however, if zinc oxide nanoparticles are used as a catalyst, the molecular weight of the resulting polymer can still be limited within 4000 g/mol. Therefore, the new catalyst can better control the molecular weights of the prepolymer and polymer, and shift the reaction equilibrium to the depolymerization reaction, thereby significantly improving the efficiency of the production of lactide.

2) Synthesis of Lactide

TABLE 3

The results of lactide synthesis in Examples 1-5

| Example No. | Catalyst | Cleavage temperature (° C.) | Reaction time (h) | Lactide produced (g) | Conversion yield (%) | Production yield (%) |
| --- | --- | --- | --- | --- | --- | --- |
| 1 | none | 180-250 | 13 | 25.27 | 48.97 | 60.77 |
| 2 | Tin (II) 2-ethylhexanoate (0.3 wt %) | 180-245 | 12 | 31.09 | 60.25 | 74.77 |
| 3 | Tin (II) 2-ethylhexanoate (0.6 wt %) | 180-245 | 10.5 | 33.13 | 64.21 | 79.68 |
| 4 | Zinc oxide aqueous nanoparticle dispersion (30-40 nm, 0.3 wt %) | 170-220 | 13.5 | 37.84 | 73.33 | 91.01 |
| 5 | Zinc oxide nanoparticle aqueous dispersion (30-40 nm, 0.6 wt %) | 170-220 | 10 | 38.36 | 74.34 | 92.26 |

According to the above-mentioned results, both the tin (II) 2-ethylhexanoate and the zinc oxide nanoparticles can catalyse the production of lactide from lactic acid. The new catalyst of zinc oxide nanoparticles has a higher catalytic efficiency than the traditional tin-based catalysts, and increases the production yield of lactide to 90% or more. Moreover, when zinc oxide nanoparticles are used as a catalyst, the required product distillation temperature is lower and the reaction time is shorter. Therefore, it can be concluded that the new catalyst (0.6 wt %) in this patent has a better catalytic effect on the synthesis of lactide and is able to increase the production yield to 92%.

3) Stability of Catalyst

The changes in the appearances of the reactants during depolymerization in Examples 3 and 5 are shown in FIG. 3. When a tin-based catalyst is used in Example 3, a very significant colour change occurs to the reactants. FIG. 3(A) shows the reaction temperature at 200° C., and FIG. 3(B) shows the reaction temperature at 250° C.; this is caused by the severe oxidation reaction of the reactants at high temperatures. However, where a zinc oxide nanoparticle aqueous dispersion as a catalyst in Example 5, only a slight oxidation phenomenon occurs. FIG. 3(C) is the case where the reaction temperature is 200° C., and FIG. 3(D) is the case where the reaction temperature is 220° C. The results show that the catalyst proposed in this patent is more stable than the traditional tin-based catalysts under high temperature conditions (≥180° C.).

4) Purification of Lactide Product

Figure 4:
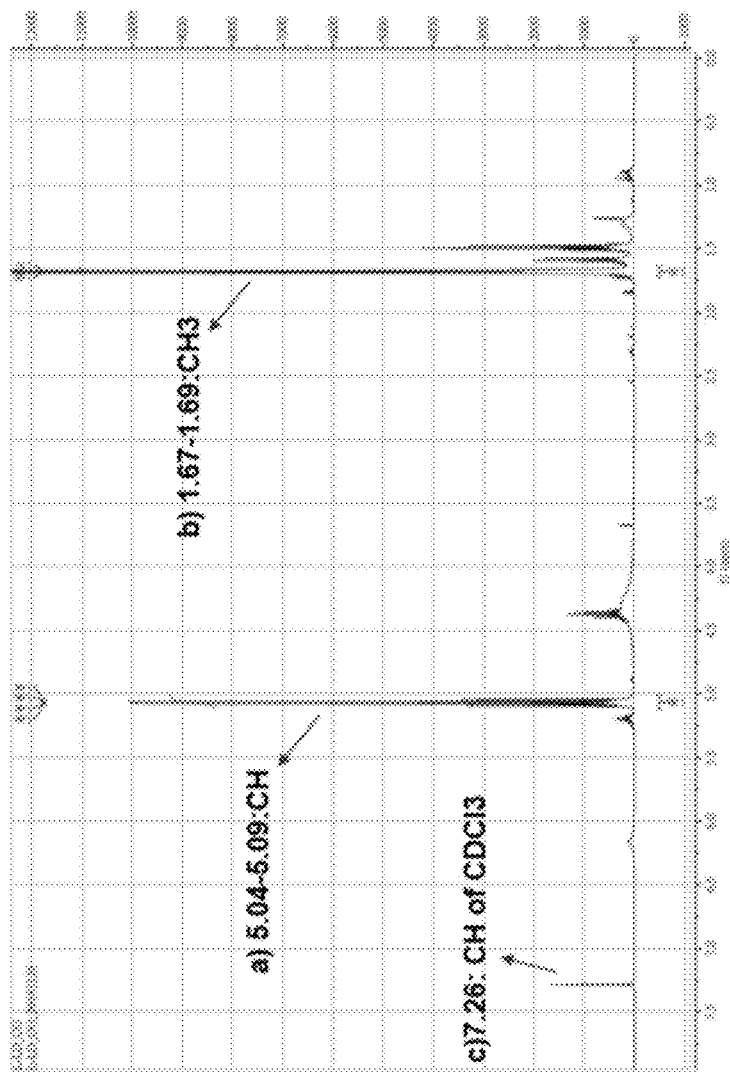
FIG. 4 is a nuclear magnetic resonance spectrum of crude lactide synthesized using the novel catalysis method in Example 5 as detected using a 1H-NMR method.
Figure 5:
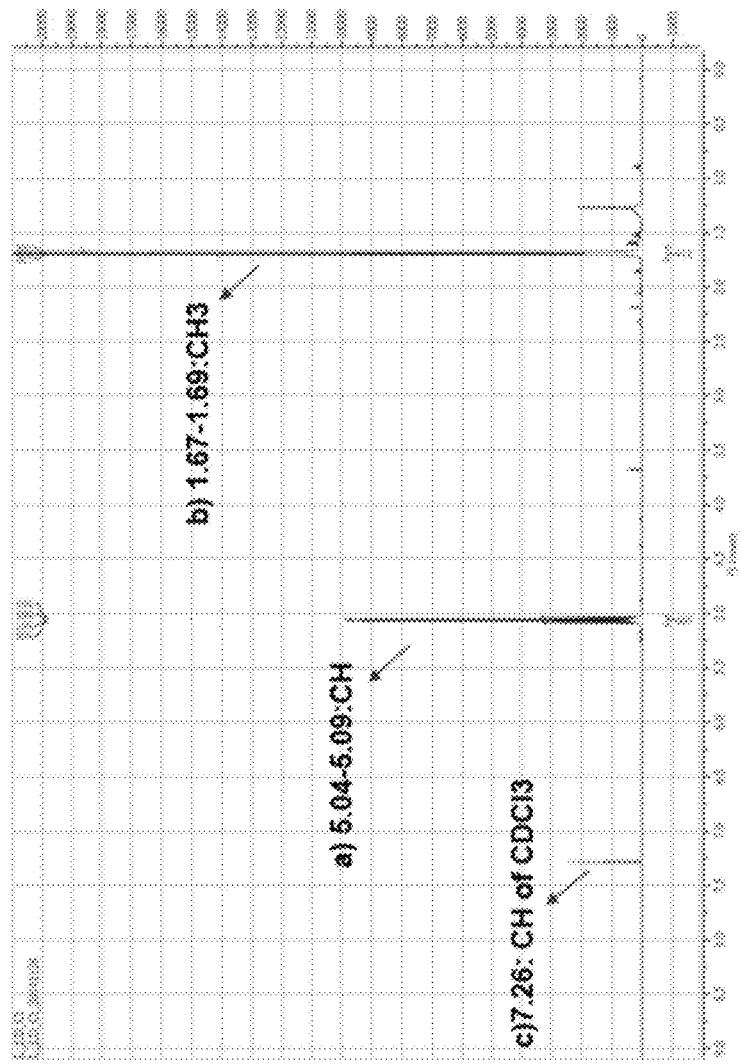
FIG. 5 is a nuclear magnetic resonance spectrum of the lactide product purified by recrystallization in ethyl acetate in Example 1 as detected using a 1H-NMR method.

FIG. 4 is a nuclear magnetic resonance spectrum of crude lactide synthesized using the novel catalysis method in Example 5 as detected using a 1H-NMR method. In the figure, the peaks of (a) CH and (b) CH3 indicate that the resulting product is lactide, and the peak of (c) CH represents solvent chloroform. The purity of crude lactide is about 85-88%;

and FIG. 5 is a curve chart of the result of the lactide purified by recrystallization in ethyl acetate in Example 5 as detected using a 1H-NMR method. In the figure, the peaks of (a) CH and (b) CH3 indicate that the resulting product is lactide, and the peak of (c) CH represents solvent chloroform. The purity of the purified lactide exceeds 99%.

It should be specially stated that the above technical solutions are only used to illustrate the present invention but are not used to limit the scope of the present invention. In addition, after reading the contents of the present invention, a person skilled in the art would be able to change or modify the present invention, and the equivalent forms are also within the scope defined by the appended claims of the present application.

The invention claimed is:

1. A method for the catalytic synthesis of lactide from lactic acid, characterized in that the synthesis of lactide from lactic acid is catalyzed solely by a zinc oxide aqueous nanoparticle dispersion.

2. The method for the catalytic synthesis of lactide from lactic acid according to claim 1, characterized in that said zinc oxide nanoparticle aqueous dispersion is a dispersion of zinc oxide nanoparticles in water; and in said zinc oxide nanoparticle aqueous dispersion, the particle size of the zinc oxide nanoparticles is 30-40 nm, and the mass percentage of the zinc oxide nanoparticles is 20%.

3. The method for the catalytic synthesis of lactide from lactic acid according to claim 1, characterized in that the method comprises the following steps:
   a. Dehydration: lactic acid and a catalyst are mixed at a ratio under the conditions of 60-80° C. and 60 kPa, and subjected to a dehydration reaction for 2 hours to remove free water from the lactic acid to obtain a dehydration product;
   b. Polymerization: said dehydration product is subjected to a polymerization reaction for 3 hours under the conditions of 120-150° C. and 10 kPa to obtain an oligomer; and
   c. Depolymerization: said oligomer is subjected to a depolymerization reaction for 3-5 hours under the conditions of 170-220° C. and 1-3 kPa.

4. The method for the catalytic synthesis of lactide from lactic acid according to claim 3, characterized in that the amount of said catalyst in dehydration step a. is 0.3-0.6% by weight of said lactic acid.

5. A method for the catalytic synthesis of lactide from lactic acid, characterized in that the catalytic synthesis of lactide from lactic acid occurs by operation of a catalyst consisting of a zinc oxide aqueous nanoparticle dispersion.

6. The method for the catalytic synthesis of lactide from lactic acid according to claim 5, characterized in that said zinc oxide nanoparticle aqueous dispersion is a dispersion of zinc oxide nanoparticles in water; and in said zinc oxide nanoparticle aqueous dispersion, the particle size of the zinc oxide nanoparticles is 30-40 nm, and the mass percentage of the zinc oxide nanoparticles is 20%.

7. The method for the catalytic synthesis of lactide from lactic acid according to claim 5, characterized in that the method comprises the following steps:
   a. Dehydration: lactic acid and a catalyst are mixed at a ratio under the conditions of 60-80° C. and 60 kPa, and subjected to a dehydration reaction for 2 hours to remove free water from the lactic acid to obtain a dehydration product;
   b. Polymerization: said dehydration product is subjected to a polymerization reaction for 3 hours under the conditions of 120-150° C. and 10 kPa to obtain an oligomer; and
   c. Depolymerization: said oligomer is subjected to a depolymerization reaction for 3-5 hours under the conditions of 170-220° C. and 1-3 kPa.

8. The method for the catalytic synthesis of lactide from lactic acid according to claim 5, characterized in that the amount of said catalyst in said dehydration step a. is 0.3-0.6% by weight of said lactic acid.

* * * * *